United States Patent [19]

Neidleman et al.

[11] 4,284,723
[45] * Aug. 18, 1981

[54] PREPARATION OF EPOXIDES AND GLYCOLS FROM GASEOUS ALKENES

[75] Inventors: Saul L. Neidleman, Oakland; William F. Amon, Jr., Danville; John Geigert, Concord, all of Calif.

[73] Assignee: Cetus Corporation, Berkeley, Calif.

[*] Notice: The portion of the term of this patent subsequent to Jan. 27, 1998, has been disclaimed.

[21] Appl. No.: 39,337

[22] Filed: May 16, 1979

Related U.S. Application Data

[63] Continuation-in-part of Ser. No. 914,384, Jun. 14, 1978, abandoned.

[51] Int. Cl.$^3$ .......................... C12P 17/02; C12P 7/18
[52] U.S. Cl. ................ 435/123; 260/348.21; 435/132; 435/155; 435/158
[58] Field of Search ............... 435/132, 155, 190, 192, 435/52, 53, 123, 157, 158, 232; 260/348.21

[56] References Cited

U.S. PATENT DOCUMENTS

| | | | |
|---|---|---|---|
| 3,455,797 | 7/1969 | Courtier | 260/348.21 X |
| 3,527,673 | 9/1970 | Neidleman | 435/52 X |
| 3,528,886 | 9/1970 | Neidleman | 435/53 |

OTHER PUBLICATIONS

Johnson, et al., Halohydrins, Chemical Abstracts, vol. 76:66700g, 1972 (p. 48).
Weigert, et al., Halohydrins, Chemical Abstracts, vol. 79:65781f, 1973 (p. 401).
Sumner, et al., Chemistry and Methods of Enzymes, Academic Press, Inc., New York, 1953 (pp. 220–226).
B. Jovek, et al., Antibacterial Activity of the Lactoperoxidase System in Milk Against Pseudomonads and Other Gram-Negative Bacteria, Applied Microbiology, 8/1975 (pp. 199–204).
May, S. W., Enzymatic Epoxidation Reactions, Enzyme Microb., vol. 1, Jan. 1979 (pp. 15–22).

*Primary Examiner*—David M. Naff
*Attorney, Agent, or Firm*—Fitch, Even, Tabin, Flannery & Welsh

[57] ABSTRACT

Epoxides or glycols are produced by passing a gaseous olefin through a reaction mixture containing a halogenating enzyme, an oxidizing agent and a halide ion source whereby the olefin is converted to a halohydrin. The halohydrin is converted to an epoxide which may be converted by hydration to a glycol. Conversion of the halohydrin to an epoxide may be carried out enzymatically.

12 Claims, No Drawings

PREPARATION OF EPOXIDES AND GLYCOLS FROM GASEOUS ALKENES

This application is a continuation-in-part of application Ser. No. 914,384, filed June 14, 1978, now abandoned. This application is related to application Ser. No. 42,219, filed May 29, 1979, now U.S. Pat. No. 4,247,641.

This invention relates generally to a process for making useful commercial products from alkenes. More particularly, the invention relates to an improved process resulting in the production of epoxides and glycols from gaseous alkenes wherein an enzyme is used to produce an intermediate halohydrin.

A number of useful chemical products, e.g. surfactants, humectants, polymers and plasticizers, are produced from gaseous, unsaturated hydrocarbons such as ethylene and propylene. Frequently such processes involve first producing an epoxide or glycol and then reacting it in some subsequent chemical process to form the desired compound. To form the epoxide two general approaches have been used traditionally. The first of these is to oxidize the alkene directly. The second is to form an intermediate halohydrin and then convert it with a base to form the epoxide. Glycols usually are produced by hydrating the corresponding epoxide. One should also note that in recent years the development of alternate processes for producing epoxides and glycols have been receiving considerable attention, due to the high commercial value of such materials.

Processes utilizing direct oxidation, currently a commercially favored path from ethylene to ethylene oxide, normally require pure oxygen and supported silver oxide catalyst, both of which add to cost and necessitate expensive safety procedures and devices. Moreover, the elevated temperature required in the process, typically 270° C., increases the energy cost in the process. Also, reaction yields are decreased by the production of substantial quantities of carbon dioxide and water as by-products.

Processes involving the production of epoxides by conversion of an intermediate halohydrin, currently a commercially favored pathway from propylene to propylene oxide, encounter problems in the formation of the halohydrin itself. Known processes for the production of halohydrins from alkenes typically involve the addition of alkene, halogen and water in a reactor under controlled conditions. Such a process frequently results in the production of undesirable side products such as hydrochloric acid (which requires neutralization), haloalkanes and bis- (haloalkyl) ethers. Moreover, use of free halogen in any process requires expensive control procedures and equipment to prevent loss of this toxic reactant. Also, the use of free halogen is now preferably avoided because of the energy-intensive process employed for its production.

It is an object of the present invention to provide an improved process for producing epoxides and glycols from gaseous alkenes.

Another object of the invention is to provide a process for producing epoxides and glycols from gaseous alkenes wherein an intermediate halohydrin is produced without the need for a gaseous free halogen.

A further object of the invention is to provide a process for the production of epoxides and glycols from gaseous alkenes which is relatively safe, low in cost, and low in energy requirements as compared with known processes.

Other objects of the present invention will become more apparent from the following detailed description and accompanying claims. In the description and claims, all proportions and percentages are by weight, all pressures are standard atmospheric, and all temperatures are in degrees centigrade, unless otherwise specified.

In general, in accordance with one aspect of the present invention, the halohydrin of a gaseous olefin is produced by introducing the gaseous olefin into a reaction mixture of a halogenating enzyme, a source of halide ion, and an oxidizing agent. The reaction of the gaseous olefin to provide the halohydrin of the olefin proceeds spontaneously and rapidly under ambient conditions of temperature and pressure. The halohydrin is then converted to the epoxide or glycol.

As used herein, the term "alkene" is intended to include all aliphatic hydrocarbons having carbon to carbon double bonds, wherein each of the carbon atoms containing the double bond is joined to either hydrogen or another carbon. Alkene is also intended to include open chain compounds having more than one double bond. The term "olefin" as used herein is intended to have the same meaning as alkene.

As used herein, the term "epoxide" as produced from a gaseous alkene includes oxides; the term "glycol" is the same as diol wherein the hydroxyl groups are on adjacent carbons.

As used herein, the term "gaseous alkene" means an alkene which is a gas, at or about standard atmospheric pressure, and at a temperature which will not destroy the enzyme. Typically, this is at or near room temperature namely, about 20° C.

Representative gaseous alkenes useful in this invention are ethylene, propylene, butene-1, cis-butene-2, trans-butene-2, 1,3-butadiene, isobutylene and allene.

The present invention makes use of certain peroxidases which have catalytic activity with respect to breaking the double bond of gaseous olefin compounds and promoting hydroxylation on one of the carbons while promoting halogenation on the adjacent carbon under particular reaction conditions. The peroxidase enzymes capable of providing catalytic activity as described herein are referred to as "halogenating enzymes".

A preferred halogenating enzyme is derived from the microorganism, *Caldariomyces fumago*. Other sources of halogenating enzyme include seaweed, milk (lactoperoxidase), thyroid (thyroid peroxidase), leukocytes (myeloperoxidase) and horseradish (horseradish peroxidase). Certain of these peroxidases are commercially available.

For ease of discussion, various aspects of the present invention will be described with particularity, but not exclusivity, in connection with use of the preferred peroxidase, chloroperoxidase, derived from *Caldariomyces fumago*. The microorganism *Caldariomyces fumago*, may be grown as a static or agitated, submerged culture in CzapekDox medium at room temperature for 3 to 10 days by conventional methods. The halogenating enzyme, chloroperoxidase, is prepared from an aqueous homogenate of the mycelial pads of the microorganism grown under static conditions or from the filtrate of the microorganism grown under static or agitated, submerged culture conditions.

The halogenating enzyme may also be used in an immobilized form. The processes for enzyme immobilization are familiar to those skilled in the art, and consist of reacting a solution of the enzyme with one of a broad range of organic and inorganic supports. Included among these are polyacrylamide, ethylene-maleic acid copolymers, methacrylic-based polymers, polypeptides, styrene-based polymers, agarose, cellulose, dextran, porous glass beads, and aluminum or titanium hydroxide. Enzymes in this form have increased stability, extended life and usefulness, and recoverability. Reactions employing immobilized enzymes may be run in columns or reaction tanks.

In addition to the halogenating enzyme, a source of inorganic halide and an oxidizing agent are required in the reaction mixture. A preferred oxidizing agent is hydrogen peroxide, which may be added directly to the mixture in a single batch addition, or in a continuous slow feed. It may alternatively be generated as a slow feed in situ by the use of a hydrogen peroxide-producing enzyme system. Such enzyme systems are well known in the art, and include glucose oxidase in the presence of glucose, D- and L-amino acid oxidases in the presence of D- or L-methionine, methanol oxidase in the presence of methanol, and diamine oxidases in the presence of histamine. The hydrogen peroxide-generating system may be present in the non-immobilized or immobilized state as with the halogenating enzyme. The hydrogen peroxide may also be generated by a chemical reaction, such as the anthraquinone or isopropyl alcohol oxidation processes.

With in situ generation of hydrogen peroxide using glucose oxidase or methanol oxidase, coproducts include gluconic acid (in the case of glucose oxidase) and formaldehyde (in the case of methanol oxidase). Although each of these coproducts is commercially useful, it is conceivable that if the method of the invention is adopted on a large scale for the production of epoxides and glycols, the amount of coproduct produced by in situ hydrogen peroxide generation could exceed market demand by a substantial amount. Under such circumstances, two possibilities are presented. The first is to find additional uses and therefore additional markets for the coproducts gluconic acid or formaldehyde. The other possibility, however, is to develop or modify the process in such a way as to produce a coproduct which is capable of being absorbed by relatively higher market demand.

It may therefore be preferable that the enzyme used for the production of hydrogen peroxide in situ be glucose-2-oxidase. Using glucose as a substrate, glucose-2-oxidase catalyzes the following reaction (volc et al, *Folia Microbiol* 23:292-298, 1978):

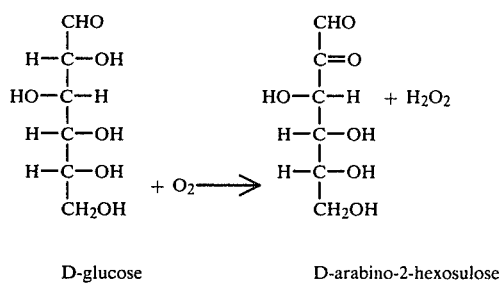

D-glucose          D-arabino-2-hexosulose

The D-arabino-2-hexosulose thus produced may be readily converted to D-fructose by simple chemical hydrogenation as follows:

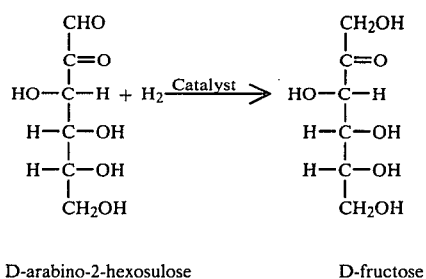

D-arabino-2-hexosulose      D-fructose

The advantage of relatively low-cost coproduction of D-fructose is the high desirability of fructose as a sweetener. The substantially higher sweetness of fructose per calorie or unit weight as compared with dextrose or sucrose offers distinct advantages for a wide variety of food applications. The current price and restricted availability of fructose, however, has limited its use. The present invention would be capable of generating large quantities of fructose at prices competitive with sucrose as currently provided.

The hydrogen peroxide is present preferably in a molar ratio of from about 0.5:1 to about 50:1, most preferably in a ratio of from about 1:1 to about 5:1 with respect to the olefin. The molar ratio preferences refer to the average presence of hydrogen peroxide during the reaction. The actual molar ratio will usually vary during the reaction and the molar ratio at any particular time may be above or below the ranges cited. Other suitable oxidizing agents include organic peroxides, such as methyl, ethyl, or butyl peroxides.

The halogen source may be any of the water soluble halide salts. The preferred halogen sources are the chloride, bromide, and iodide salts of the alkali metals, sodium and potassium. The salts are present in the reaction mixture at a level sufficient to provide a slight excess of halide ion with respect to the stoichiometric amount required for the reaction.

The reaction is conducted within the pH range of from about 2.2 to about 8.0. The pH of the reaction may be maintained within the desired range by use of a buffering agent. Suitable buffers include sodium or potassium phosphate, gluconate, citrate, formate, and acetate based systems. Other suitable techniques besides buffering may be used for pH control and adjustment. While the reaction is preferably conducted under aerobic conditions in an aqueous medium it can also be conducted in the presence of low levels of organic solvents, such as the lower aliphatic alcohols, ketones, dioxane, or dimethylformamide to increase substrate solubility.

A resulting intermediate product in the method of the present invention is a halohydrin represented by the following structure:

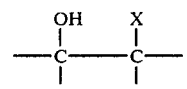

X = halogen

The halogen is predominantly attached to the carbon atom that yields the least stable carbonium ion. Thus, from monoolefinic gaseous hydrocarbons such as 1-olefins, there is obtained 1-halo-2-hydroxy hydrocarbons (major) and 2-halo-1-hydroxy hydrocarbons (minor):

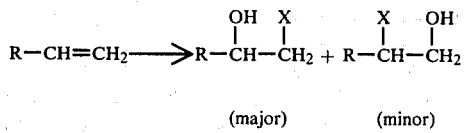

(major)    (minor)

From polyolefinic gaseous hydrocarbons, there may be obtained both monohalohydrins and polyhalohydrins, as in the case of 1,3-butadiene:

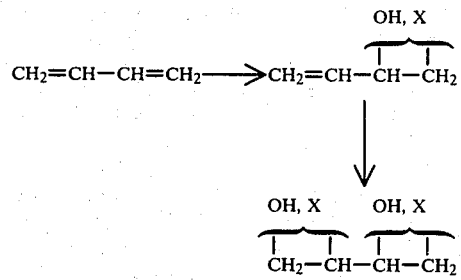

From gaseous olefins containing cumulative double bonds, there may be obtained both monohalohydrins and polyhalohydrins, as in the case of allene:

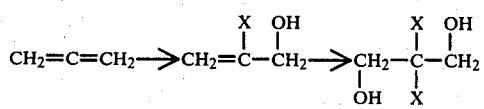

The components other than the gaseous olefins, namely the halogenating enzyme, the oxidizing agent, the halide ion source and the buffer agent, are simply mixed together in water or mixed aqueous and organic media to provide a reaction mixture. It is a surprising and important result of the present invention that gaseous olefins, such as ethylene or propylene, can be reacted by simply passing the gaseous olefins through the reaction mixture.

The halohydrins formed by the reaction are easily converted to the oxide, which may itself be useful or which may be converted to a glycol or other useful derivative of the olefin in accordance with conventional procedures. To convert the halohydrin to an epoxide, any of several techniques may be employed. For example, the halohydrin may be converted to the epoxide by contacting with an aqueous slurry of slaked lime. Hydration of the epoxide results in the glycol.

Other techniques may employ an enzyme to effect conversion of the halohydrin to an epoxide. One such enzyme is the halohydrin epoxidase of a *Flavobacterium* sp. cited in the example below. Similar activity has been detected in a variety of other organisms such as the seaweed *Laurencia pacifica*, and the yeast, *Hansenula polymorpha*. The enzyme carries out the following reaction:

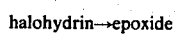

Specifically for propylene bromohydrin:

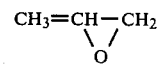

In this case, both steps of the method of the invention may be carried out sequentially or even simultaneously in the same reactor.

The following examples illustrate various features of the invention, but are in no way intended to limit the scope of the invention which is defined in the appended claims. In many of the examples, preparation of only the intermediate halohydrins is discussed, since conversion of the halohydrin to the epoxide can be achieved in all cases by suitable procedures such as alkaline or enzymatic treatment.

EXAMPLES 1-18

Dilute hydrogen peroxide (1 mg/ml final), halide salt (10 mg/ml final) and 0.1 M potassium phosphate buffer are mixed together in a 100 milliliter Pyrex flask at room temperature and room pressure. The halogenating enzyme is added and the olefin is bubbled into the reaction mixture. Sample is withdrawn at 30 minutes and analyzed for halohydrin.

The halogenating enzymes are prepared as follows:

Chloroperoxidase (CP). Mycelial pads of *Caldariomyces fumago* (ATCC 16373) are grown on potato agar slants as follows: Sliced potato (200 g) is cooked in distilled water (500 ml) for 40 minutes and then strained. A solution of glucose (21 g) and agar (20 g) in distilled water (500 ml) is added to the strained solution. The pH is adjusted to 6.8 and the volume is brought to 1 liter with distilled water. The medium is sterilized at 121° for 15 minutes. The organism is inoculated on the potato agar slants, produced in accordance with the above procedure, and is grown for about one week at room temperature. The organism is then used to inoculate the soybean-glucose medium (50 ml) prepared as follows: to 1 liter of distilled water are added extraction process soybean meal (30 g), glucose (30 g), and CaCO$_3$ (7 g). The medium is sterilized at 121° for 30 minutes and is then inoculated with the organism after cooling. The organism is grown for 4-5 days on a rotary shaker at 25°. 5 ml of this material is used to inoculate a 500 ml Erlenmeyer flask containing 100 ml of a modified Czepek-Dox medium prepared by adding the following to 1 liter of distilled water: NaNO$_3$ (3 g), KH$_2$PO$_4$ (1 g), KCl (0.5 g), MgSO$_4$.7H$_2$O (10 mg) and glucose (40 g). The medium is sterilized at 121° for 20 minutes prior to inoculation with the organism. The organism is grown under static conditions at room temperature 5-7 days. The black mycelial pads which form are collected, rinsed with distilled water, and stored in plastic bags in a freezer at −10° for subsequent use.

The halogenating enzyme is prepared by grinding 6 mycelial pads (prepared in accordance with the above procedures) with 60 g acid-washed sand and 60 ml distilled water for 2 minutes in a Virtis 45 homogenizer. The homogenate is centrifuged while cold and the supernatant solution filtered through Whatman #1 paper at room temperature. The filtrate is concentrated about 10-fold using a rotary film evaporator at reduced pressure and temperature less than 35°. The concentrate is chilled at 0° in an ice bath, and prechilled (0°) ethanol is added until 45% ethanol (v/v) is reached. The mixture is stirred vigorously for 15 minutes, and then centrifuged at −10° (at 15,000 g) with a 55-34 rotor in a Sorval RC-5 Superspeed for 15 minutes. The black sediment is discarded. To the centrifugate, cooled at 0°, is added additional prechilled ethanol to give 65% ethanol (v/v). The mixture is slowly stirred for 30 minutes at 0°, and then centrifuged as before. The centrifugate is discarded, and the precipitate containing the chloroperoxidase activity is dissolved in a minimum volume of 0.05 M potassium buffer (pH 7). The enzyme solution is stored at −20°. The activity is measured as 80 monochlorodimedon units/ml. (Ref: Morris, D. R. and Hager, L. P., *J. Biol. Chem.*, 241, 1763 (1966)).

Lactoperoxidase (LP)

Purchased from Sigma Chemical Company (Catalogue #L-7129).

Seaweed Peroxidase[1](SWP[1])

*Laurencia pacifica* obtained along the coast of La Jolla, Calif., is prepared by grinding and dispersing 5 g of the seaweed in 10 ml of 0.3 M potassium phosphate buffer (pH 6.0) for 2 minutes in a Virtis 45 homogenizer.

Seaweed Peroxidase[2](SWP[2])

*Coralina* sp. obtained along the coast of La Jolla, Calif. is ground in a Virtis 45 homogenizer for 5 minutes in distilled water. The homogenate is spun at 20,000 rpm for 20 minutes. The supernatant is decanted and saved. The pellet is resuspended in distilled water and recentrifuged. This supernatant and previous supernatant are combined. The solution is brought first to 33%, then to 55% saturation in ammonium sulfate. Centrifugation and separation of pellet is performed at each step. The 33%–55% pellet fraction is passed through a DEAE column using a 0.3 M to 1 M phosphate buffer (pH 6.0) gradient. The fraction which elutes at 1 M is dialyzed against 20 mM phosphate buffer (pH 6) overnight. This preparation is stored at −20° until needed. The activity is measured as 2 monochlorodimedon units/ml.

Horseradish Peroxidase (HRP)

Purchased from Sigma Chemical Company (Catalogue #P-8250).

The halohydrins are identified by gas chromatography/mass spectrometry. The halohydrin and its corresponding epoxide (after treatment of the halohydrin with base) are compared with authentic samples. The analysis of propylene bromohydrin illustrates the procedure:

10 μl of the reaction mixture was injected into a Perkin Elmer Model 3920 gas chromatograph, equipped with a 6 foot by ⅛ inch coiled, stainless steel column, packed with Porapak R (80/100 mesh), and attached to a Dupont Model 21-491 mass spectrometer operating at 70 eV ionization. Flow rate was set at 30 ml/minute for helium and the column temperature was programmed for 185° C. at 220° C. at a rate of 1° C./minute. Retention times for the propylene bromohydrins were 9 minutes for 1-bromo-2-propanol and 10 minutes for 2-bromo-1-propanol.

Product identity was confirmed by comparison with authentic samples of propylene bromohydrin: 1-bromo-2-propanol was purchased from Pfaltz and Bauer, Inc.; 2-bromo-1-propanol was synthesized by lithium aluminum hydride reduction of 1-bromopropionyl chloride. The reaction products and the authentic samples showed the same retention times and identical mass spectra: bromine was identified by the presence of the M and M+2 isotope clusters of equal intensity; the molecular ion for both isomers was confirmed by chemical ionization with isobutane reagent gas (M+; m/e 138+140); for 1-bromo-2-propanol the major fragmentation was the expected loss of $CH_2Br$ while for 2-bromo-1-propanol the major fragmentation was the expected loss of $CH_3CHBr$.

Further, both bromohydrins were converted to propylene epoxide by addition of 10% sodium hydroxide to their aqueous solutions to yield a pH greater than 10. Identity of propylene epoxide was confirmed by gas chromatography/mass spectrometry comparison with an authentic sample (purchased from Aldrich Chemical Company, Inc.). The reaction product after base treatment and the authentic sample showed the same retention time (2 minutes) and identical mass spectra (M+·; m/e 58).

Variable conditions and results are set forth in Table I.

The reactions are found clean, i.e., no detected halogenated by-product formation.

TABLE I

| Ex. | Olefin | Halide | Enzyme | (Units) | pH | Halohydrin Produced | (mg/ml) |
|---|---|---|---|---|---|---|---|
| 1 | Ethylene | KCl | CP | (10) | 3 | 2-chloroethanol | (0.1) |
| 2 | Ethylene | KBr | CP | (10) | 3 | 2-bromoethanol | (1.8) |
| 3 | Ethylene | KBr | LP | (50) | 6 | 2-bromoethanol | (0.5) |
| 4 | Propylene | KCl | CP | (10) | 3 | 1-chloro-2-propanol + 2-chloro-1-propanol (90:10) | (0.1) |
| 5 | Propylene | KCl | LP | (50) | 6 | 1-chloro-2-propanol + 2-chloro-1-propanol (90:10) | (0.3) |
| 6 | Propylene | KBr | CP | (10) | 3 | 1-bromo-2-propanol + 2-bromo-1-propanol (90:10) | (1.5) |
| 7 | Propylene | KBr | CP | (10) | 4.5 | 1-bromo-2-propanol + 2-bromo-1-propanol (90:10) | (0.5) |
| 8 | Propylene | KBr | LP | (50) | 6 | 1-bromo-2-propanol + 2-bromo-1-propanol (90:10) | (1.0) |
| 9 | Propylene | KBr | SWP[1] | (1) | 6 | 1-bromo-2-propanol + 2-bromo-1-propanol (90:10) | (0.2) |
| 10 | Propylene | KBr | SWP[2] | (1) | 6 | 1-bromo-2-propanol + 2-bromo-1-propanol (90:10) | (0.03) |
| 11 | Propylene | KI | CP | (10) | 3 | 1-iodo-2-propanol + 2-iodo-1-propanol (90:10) | (1.5) |
| 12 | Propylene | KI | HRP | (5) | 6 | 1-iodo-2-propanol + 2-iodo-1-propanol (90:10) | (0.3) |
| 13 | Butene-1 | KBr | CP | (10) | 3 | 1-bromo-2-butanol + 2-bromo-1-butanol | (0.5) |
| 14 | Isobutylene | KBr | CP | (10) | 3 | 1-bromo-2-methyl-2-propanol | (0.5) |
| 15 | cis-Butene-2 | KBr | CP | (10) | 3 | 3-bromo-2-butanol | (0.6) |
| 16 | trans-Butene-2 | KBr | CP | (10) | 3 | 3-bromo-2-butanol | (0.6) |
| 17 | Allene | KBr | CP | (10) | 3 | 2-bromo-2-propen-1-ol | (0.4) |
| 18 | 1,3-Butadiene | KBr | CP | (10) | 3 | 1-bromo-3-buten-2-ol + 2-bromo-3-buten-1-ol + 1,4-dibromo-2,3-butanediol (98:1:1) | (2.6) |

EXAMPLE 19

The procedure of Examples 2 and 6 are followed substituting a mixed ethylene-propylene stream for the single olefin.

The result is 1.4 mg/ml of 2-bromoethanol and 0.9 mg/ml of 1-bromo-2-propanol+2-bromo-1-propanol (90:10).

EXAMPLE 20

The importance of immobilizing the halogenating enzyme and using a slow feed of $H_2O_2$ by in situ enzymatic generation are shown in this example. Halide salt (10 mg/ml final) and 0.1 M potassium phosphate buffer (pH 6) are mixed together in four 100 milliliter Pyrex flasks at room temperature and room pressure. Propylene is bubbled into the reaction mixtures. Sample is withdrawn at 60 minutes and analyzed for halohydrin. The variable conditions and the results are set forth in Table II. These results indicate that the use of immobilized halogenating enzyme coupled with a slow feed (slow to the point of use as generated) of $H_2O_2$ greatly improves the production of propylene bromohydrins, from which propylene oxide is easily obtained.

TABLE II

| Re-action | $H_2O_2$ Feed | Lactoperoxidase | Propylene Bromohydrin Yield mg/ml |
|---|---|---|---|
| 1 | Direct addition[1] | Non-immobilized[3] | .008 |
| 2 | Direct addition[1] | Immobilized[4] | .03 |
| 3 | In situ generation[2] | Non-immobilized[3] | .21 |
| 4 | In situ generation[2] | Immobilized[4] | 1.51 |

Footnotes:
[1] 1 mg/ml $H_2O_2$ final
[2] 0.2 ml of 1.0M α-D-glucose and 0.1 ml of glucose oxidase (Sigma Chemical Corp., Catalogue #G-6500) per 10 ml of reaction mixture.
[3] from P.L. Biochemicals, Inc., 20 units added.
[4] from P.L. Biochemicals, Inc., bound to Sepharose, 20 units added.

EXAMPLE 21

The use of immobilized seaweed peroxidase is shown in this example.

The immobilized seaweed peroxidase is prepared as follows:

Glass beads (obtained from Sigma Chemical Company, PG-700-200) are activated by suspending 1 g of glass beads in 18 ml of deionized water. 2 ml of 10% (v/v) α-aminopropyltriethyoxyl silane are added and the pH of the mixture is adjusted to 3-5 with 6 N HCl. The mixture is shaked at 75° C. for 2 hours. The glass beads are then vacuum dried overnight at 80° C. 3.2 ml of purified *Coralina* sp. enzyme, prepared as in Examples 1-18, and 50 mg of water soluble carbodiimide are added to the glass beads. The pH is adjusted to 4.5, and the mixture is then shaken at 4° C. overnight. The product—enzyme coated beads—is washed with water. The activity is measured as 2 monochlorodimedon units/g. of beads.

A reaction using 1 g of the seaweed peroxidase coated glass beads is run as in Example 20, reaction 4, with these modifications.

(a) 40 mg/ml KBr final
(b) 50 mg/ml α,D-glucose
(c) 1.0 ml of glucose oxidase

The result is:

| Reaction time, hour | Propylene Bromohydrin (mg/ml) |
|---|---|
| 4 | 9.0 |
| 8 | 13.3 |
| 10 | 16.5 |
| 21 | 24.1 |

EXAMPLE 22

The procedure of Example 21 is followed substituting KI for KBr.

The result is 3.0 mg/ml of propylene iodohydrin at 1 hour.

EXAMPLE 23

The use of cells of *Hansenula polymorpha* ATCC 26012 as a source of methanol oxidase to generate $H_2O_2$ is shown in this example.

Cells of the microorganism are prepared as follows:

The culture is maintained on agar slants at 37°, with periodic transfer. The composition of the agar medium per liter is $NaNO_3$ (3 g), KCl (0,5 g), $MgSO_4.7H_2O$ (0.5 g), acidified 1% $FeSO_4.7H_2O$ (1 ml), $KH_2PO_4$ (1 g), glucose (40 g), NaCl (32.14 g), yeast extract (2 g), and agar (15 g). pH is adjusted to 6.0 with 10% NaOH prior to sterilization under standard conditions. Growth of the culture to be used as a source of methanol oxidase activity is carried out on a medium of the following composition per liter: $(NH_4)_2HPO_4$ (6 g), $MgSO_4.7H_2O$ (2 g), and yeast extract (5 g). pH is adjusted to 5.0 with 85% $H_3PO_4$ prior to sterilization under standard conditions. Fermentations are run in 125 ml Erlenmeyer flasks containing 20 ml of this medium to which 1.0 ml sterile methanol is added. The fermentations are performed at 37°, 200 rpm on a New Brunswick shaker, 2"-throw, for 1-3 days. The cells are harvested by centrifugation, washed once with 0.1 M phosphate buffer and then resuspended at 1/5 the original fermentation volume in 0.1 M phosphate buffer, pH 6.0. The cells are stored in the refrigerator at 4° C. for up to one week without substantial loss of activity.

A reaction with lactoperoxidase is run as in Example 20, reaction 3 with these modifications:

(a) 0.1 ml 3% methanol instead of 0.1 ml 1 M α-D-glucose.

(b) 1 ml of above-described suspension of cells of *Hansenula polymorpha* ATCC instead of 0.1 ml glucose oxidase.

The reaction mixture is analyzed for propylene bromohydrins after 60 minutes. The total yield is 175 µg/ml.

EXAMPLE 24

The ability to convert propylene to propylene epoxide, enzymatically, without isolation of the intermediate halohydrin is shown in this Example. *Flavobacterium* sp. (Cetus #5095) contains a halohydrin epoxidase, which converts halohydrins to epoxides.

The microorganism is grown at 25°, 200 rpm 2"-throw on a New Brunswick shaker in a medium reported in the literature (C. E. Castro and E. W. Bartnicki, *Biochemistry*, 7:3213 (1968)). 100 ml of medium is used per 500 ml Erlenmeyer flask. The microorganism is maintained on slants using an agarized version of the liquid medium. The seed stage is usually 48 hours. The cells for use in the conversion reaction are then grown for an additional 2-3 days, using a 1-5% inoculum from the seed stage.

A washed cell preparation of the microorganism is prepared by standard procedures and is finally resuspended at a twenty-fold concentration (as compared to the concentration in the growth stage flasks) in the appropriate phosphate buffer. Dry weight of cells in these washed cell suspensions is 15 mg/ml.

The procedure of Example 8 is followed, with the addition of 30 mg of *Flavobacterium* sp. cells to the reaction mixture.

The results obtained are 0.2 mg/ml propylene bromohydrin and 0.3 mg/ml propylene epoxide.

EXAMPLE 25

The procedure of Example 24 is followed except ethylene is substituted for propylene and chloroperoxidase (2 units) is substituted for lactoperoxidase.

The results obtained are 100 μg/ml ethylene bromohydrin and 5 μg/ml ethylene epoxide.

EXAMPLE 26

The ability to produce propylene oxide from propylene in an integrated immobilized enzyme/cell system in a continuous-flow column configuration is demonstrated in this example. The general conversion proceeds in the following manner:

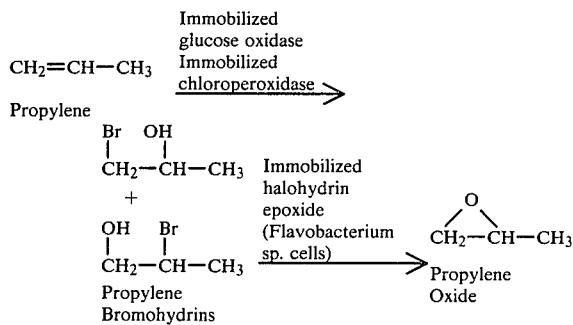

By way of example, the glucose oxidase can be covalently immobilized with AH-Sepharose 4B; the chloroperoxidase can be ionically immobilized on DEAE-sephadex A50 beads, and the halohydrin epoxidase can be insolubilized inside the cells with polyacrylamide gel.

By way of example, one column configuration includes a first region which contains the initial mixture (50 ml) of reaction components: propylene gas continuously bubbled in, 0,42 M KBr, 0.01 M glucose, and phosphate buffer (pH 4.4, 0.3 M). The mixture is slowly dripped onto a column of immobilized chloroperoxidase (CP) and glucose oxidase (GO) prepared by mixing 5 ml CP-beads and 1 ml GO-beads. This is the first stage of the system to produce propylene bromohydrin.

The details of immobilizing glucose oxidase and chloroperoxidase follow:

The glucose oxidase (1460 units/ml) is purchased from Sigma Chemical Company. The insoluble beads of AH-Sepharose 4B are obtained from Pharmacia Fine Chemical Company. Both enzyme and beads are adjusted to pH 5.0. To immobilize the enzyme onto the beads, 10 ml glucose oxidase and 10 ml beads are mixed. The coupling reaction is initiated by the addition of 2 ml N-cyclohexyl-N'(2-(4-methyl-morpholino)-ethyl)carbodiimide solution (100 mg/2 ml). The reaction mixture is incubated at 4° C. overnight. The beads are then washed with 0.03 M phosphate buffer (pH 4.4). The glucose oxidase-AH-Sepharose 4B beads are stored at 4° C. for use.

The chloroperoxidase (prepared as in Examples 1–18) is immobilized by mixing equal volume dialyzed chloroperoxidase with hydrated DEAE-Sephadex A50 beads. The enzyme beads complex are washed three times with 0.03 M phosphate buffer (pH 4.4). The activity of the beads is estimated to be 2.17 units/ml with monochlorodimedon assay. The immobilized chloroperoxidase is stored at 4° C. for future use.

The resulting eluate, containing excess reagents as well as propylene bromohydrins and gluconic acid, is adjusted to pH 6 with phosphate buffer (pH 6, 1.0 M) to allow for substantial activity with halohydrin epoxidase contained in the next column region. The immobilization of halohydrin epoxidase is performed by immobilizing the intact cells of *Flavobacterium* sp. (prepared as in Example 24) with the following reaction mixture:

| | |
|---|---|
| Flavobacterium sp. | 4 gm (wet weight) |
| Saline Solution | 4 ml |
| Acrylamide monomer | 750 mg |
| Bis-acrylamide | 40 mg |
| TEMED | 25 λ |
| Ammonium persulfate | 0.5 ml (2.5%) |

The polymerized gel is then blended into beads with a Waring blender (low speed, 20 seconds), This is the second stage of the system, producing propylene oxide from the propylene bromohydrins of the first stage.

The results obtained are 75 μg/ml propylene bromohydrin and 5 μg/ml propylene epoxide at a flow rate through the column of 1 ml/hour.

It may be seen, therefore, that the method of the invention is capable of producing epoxides and glycols from gaseous alkenes with minimum energy requirements, relatively high safety, and relatively low cost. Various modifications of the invention will become apparent to those skilled in the art from the appended claims.

What is claimed is:

1. A method for the manufacture of epoxides or glycols from a gaseous olefin selected from the group consisting of ethylene, propylene, isobutylene, butene-1, cis-butene-2, trans-butene-2, allene, and 1,3-butadiene, said method comprising providing in a reactor, a reaction mixture of a halogenating enzyme, an oxidizing agent, and a halide ion source, passing the gaseous olefin continuously through said reaction mixture to convert said olefin to a halohydrin, and converting said halohydrin to an epoxide enzymatically.

2. A method in accordance with claim 1 wherein said halogenating enzyme is a peroxidase derived from a source selected from the group consisting of the microorganism *Caldariomyces fumago*, seaweed, milk, thyroid, leukocytes and horseradish.

3. A method in accordance with claim 1 wherein said oxidizing agent is hydrogen peroxide.

4. A method in accordance with claim 1 wherein said halide ion source is a water soluble halide salt.

5. A method in accordance with claim 1 wherein the reaction is conducted within the pH range of from about 2.2 to about 8.0.

6. A method in accordance with claim 3 wherein said hydrogen peroxide is present during said reaction at a molar ratio of from about 0.5:1 to about 50:1 with respect to said olefin.

7. A method in accordance with claim 3 wherein said hydrogen peroxide is generated in situ.

8. A method according to claim 1 wherein said oxidizing agent is hydrogen peroxide generated in situ by means of methanol oxidase on a methanol substrate with coproduction of formaldehyde.

9. A method according to claim 1 wherein said oxidizing agent is hydrogen peroxide generated in situ by means of glucose oxidase on a glucose substrate with coproduction of gluconic acid.

10. A method in accordance with claim 1 wherein said halogenating enzyme is derived from a source selected from the group consisting of the microorganism *Caldariomyces fumago,* milk, and seaweed; said oxidizing agent is hydrogen peroxide; said halide ion source is selected from the group consisting of the chloride, bromide and iodide salts of sodium and potassium; and said reaction takes place in an essentially aqueous environment at ambient conditions of temperature and pressure.

11. A method in accordance with claim 1 wherein said epoxide is converted by hydration to a glycol.

12. A method in accordance with claim 1 wherein said halohydrin is converted to an epoxide in the same reactor in which said halohydrin is formed.

* * * * *